(12) United States Patent
Burrell et al.

(10) Patent No.: US 7,137,968 B1
(45) Date of Patent: Nov. 21, 2006

(54) TRANSCUTANEOUS MEDICAL DEVICE DRESSINGS AND METHOD OF USE

(75) Inventors: Robert Edward Burrell, Sherwood Park (CA); Hua Qing Yin, Sherwood Park (CA)

(73) Assignee: Nucryst Pharmaceuticals Corp., Fort Saskatchewan (CA)

( * ) Notice: Subject to any disclaimer, the term of this patent is extended or adjusted under 35 U.S.C. 154(b) by 0 days.

(21) Appl. No.: 09/524,027

(22) Filed: Mar. 13, 2000

(51) Int. Cl.
*A61M 5/32* (2006.01)
*A61F 13/00* (2006.01)

(52) U.S. Cl. .................................. 604/180; 602/54
(58) Field of Classification Search ............ 602/41–59; 128/888, 889; 604/174, 177, 179, 180, 192, 604/19; 424/443–444
See application file for complete search history.

(56) References Cited

U.S. PATENT DOCUMENTS

| | | | |
|---|---|---|---|
| 3,757,786 | A | 9/1973 | Smith |
| 3,800,792 | A | 4/1974 | McKnight et al. |
| 3,918,446 | A | 11/1975 | Buttaravoli |
| 4,059,105 | A | 11/1977 | Cutruzzula et al. |
| 4,324,237 | A | 4/1982 | Buttaravoli |
| 4,355,636 | A | 10/1982 | Oetjen et al. |
| 4,476,590 | A | 10/1984 | Scales et al. |
| 4,581,028 | A | 4/1986 | Fox, Jr. et al. |
| 4,596,556 | A | 6/1986 | Morrow et al. |
| 4,633,863 | A | 1/1987 | Filips et al. |
| 4,738,257 | A * | 4/1988 | Meyer et al. |
| 4,749,572 | A | 6/1988 | Ahari |
| 4,790,824 | A | 12/1988 | Morrow et al. |

(Continued)

FOREIGN PATENT DOCUMENTS

CA    2242033    3/1999

(Continued)

OTHER PUBLICATIONS

Burrell et al., "Efficacy of Silver-Coated Dressings as Bacterial Barriers in a Rodent Burn Sepsis Model", *WOUNDS: A Compendium of Clinical Research and Practice* vol. 11, No. 4 Jul./Aug. 1999.

(Continued)

*Primary Examiner*—Kim M. Lewis
(74) *Attorney, Agent, or Firm*—Fish & Richardson P.C.

(57) ABSTRACT

A transcutaneous device dressing and method for its use with a transcutaneous medical device, such as an intravascular catheter, which punctures the skin of a patient and which has a portion of the medical device protruding from the skin which can lead to infection. The dressing includes a top and a bottom dressing, both being formed from a flexible material and having upper and lower surfaces, with the lower surface being the skin facing surface in use. The bottom dressing has a slit formed therein extending from one edge inwardly to a termination point within the confines of the bottom dressing. An anti-microbial material is provided without the use of adhesives at the upper and lower surfaces of the bottom dressing, and at least at the lower surface of the top dressing. In use, the bottom dressing is placed next to the skin, the slit allowing the bottom dressing to surround the puncture site such that the lower surface of the bottom dressing is in contact with the skin while the upper surface of the bottom dressing is in contact with a portion of the medical device protruding from the skin. The top dressing is placed above the puncture site such that its lower surface is in contact with a portion of the medical device protruding from the skin. In this way, there is exposure of the portion of the medical device protruding from the skin to the anti-microbial activity of the anti-microbial material.

46 Claims, 2 Drawing Sheets

U.S. PATENT DOCUMENTS

| | | | |
|---|---|---|---|
| 4,803,066 A | 2/1989 | Edwards | |
| 4,828,832 A | 5/1989 | De Cuellar et al. | |
| 4,847,049 A | 7/1989 | Yamamoto | |
| 4,952,411 A | 8/1990 | Fox, Jr. et al. | |
| 4,960,413 A | 10/1990 | Sagar et al. | |
| 5,019,096 A | 5/1991 | Fox, Jr. et al. | |
| 5,064,413 A | 11/1991 | McKinnon et al. | |
| 5,122,418 A | 6/1992 | Nakane et al. | |
| 5,143,717 A | 9/1992 | Davis | |
| 5,236,421 A | 8/1993 | Becher | 604/180 |
| 5,270,358 A | 12/1993 | Asmus | |
| 5,312,335 A | 5/1994 | McKinnon et al. | |
| D349,958 S | 8/1994 | Hollis et al. | |
| 5,369,155 A | 11/1994 | Asmus | |
| 5,372,589 A | 12/1994 | Davis | 604/180 |
| 5,383,851 A | 1/1995 | McKinnon, Jr. et al. | |
| 5,399,163 A | 3/1995 | Peterson et al. | |
| 5,454,886 A | 10/1995 | Burrell et al. | 148/565 |
| 5,454,889 A | 10/1995 | McNicol et al. | 149/7 |
| 5,457,015 A | 10/1995 | Boston | |
| 5,520,639 A | 5/1996 | Peterson et al. | |
| 5,534,288 A | 7/1996 | Gruskin et al. | |
| 5,563,132 A | 10/1996 | Bodaness | |
| 5,569,207 A | 10/1996 | Gisselberg et al. | 604/175 |
| 5,578,073 A | 11/1996 | Haimovich et al. | |
| 5,631,066 A | 5/1997 | O'Brien | |
| 5,681,575 A | 10/1997 | Burrell et al. | 424/423 |
| 5,744,151 A | 4/1998 | Capelli | |
| 5,753,251 A | 5/1998 | Burrell et al. | 424/426 |
| 5,770,255 A | 6/1998 | Burrell et al. | 427/2.1 |
| 5,770,258 A | 6/1998 | Takizawa | 427/64 |
| 5,792,793 A | 8/1998 | Oda et al. | |
| 5,837,275 A | 11/1998 | Burrell et al. | 424/409 |
| 5,848,995 A | 12/1998 | Walder | 604/265 |
| 5,895,419 A | 4/1999 | Tweden et al. | |
| 5,899,880 A | 5/1999 | Bellhouse et al. | |
| 5,945,032 A | 8/1999 | Breitenbach et al. | |
| 5,958,440 A | 9/1999 | Burrell et al. | 424/409 |
| 5,981,822 A | 11/1999 | Addison | 602/41 |
| 5,985,308 A | 11/1999 | Burrell et al. | 424/426 |
| 6,010,478 A | 1/2000 | Bellhouse et al. | |
| 6,013,050 A | 1/2000 | Bellhouse et al. | |
| 6,017,553 A | 1/2000 | Burrell et al. | 424/405 |
| 6,022,547 A | 2/2000 | Herb et al. | |
| 6,071,541 A | 6/2000 | Murad | |
| 6,071,543 A | 6/2000 | Thornfeldt | |
| 6,096,002 A | 8/2000 | Landau | |
| 6,123,925 A | 9/2000 | Barry et al. | |
| 6,126,931 A | 10/2000 | Sawan et al. | |
| 6,165,440 A | 12/2000 | Esenaliev | |
| 6,187,290 B1 | 2/2001 | Gilchrist et al. | |
| 6,197,351 B1 | 3/2001 | Neuwirth | |
| 6,201,164 B1 | 3/2001 | Wulff et al. | |
| 6,224,898 B1 | 5/2001 | Balogh et al. | |
| 6,238,686 B1 | 5/2001 | Burrell et al. | 424/423 |
| 6,258,385 B1 | 7/2001 | Antelman | |
| 6,277,169 B1 | 8/2001 | Hampden-Smith et al. | |
| 6,294,186 B1 | 9/2001 | Beerse et al. | |
| 6,333,093 B1 | 12/2001 | Burrell et al. | 428/194 |
| 6,365,130 B1 | 4/2002 | Barry et al. | |
| 6,720,006 B1 | 4/2004 | Hanke et al. | |
| 2001/0010016 A1 | 7/2001 | Modak et al. | |
| 2002/0001628 A1 | 1/2002 | Ito | |
| 2002/0016585 A1 | 2/2002 | Sachse | |
| 2002/0025344 A1 | 2/2002 | Newman et al. | |
| 2002/0045049 A1 | 4/2002 | Madsen | |
| 2002/0051824 A1 | 5/2002 | Burrell et al. | 424/618 |
| 2002/0192298 A1 | 12/2002 | Burrell et al. | 424/618 |

FOREIGN PATENT DOCUMENTS

| | | |
|---|---|---|
| CN | 1082645 | 2/1994 |
| CN | 1241662 | 1/2000 |
| CN | 1262093 | 8/2000 |
| CN | 1279222 | 1/2001 |
| CN | 1291666 | 4/2001 |
| CN | 1291667 | 4/2001 |
| CN | 1306117 | 8/2001 |
| CN | 1322874 | 11/2001 |
| CN | 1328819 | 1/2002 |
| CN | 1328827 | 1/2002 |
| DE | 2748882 A1 | 5/1979 |
| DE | 3807944 A1 | 9/1989 |
| DE | 195 41 735 A | 5/1997 |
| DE | 195 41 735 A1 | 5/1997 |
| EP | 0 136 768 | 4/1985 |
| EP | 0 254 413 | 1/1988 |
| EP | 0 356 060 | 8/1989 |
| EP | 0 355 009 | 2/1990 |
| EP | 0 378 147 | 7/1990 |
| EP | 0 599 188 | 6/1994 |
| EP | 0 681 841 A | 11/1995 |
| EP | 0681841 | 11/1995 |
| EP | 0780138 A1 | 6/1997 |
| EP | 0 328 421 A2 | 8/1999 |
| EP | 1 159 972 | 12/2001 |
| GB | 420052 | 11/1934 |
| GB | 427106 | 4/1935 |
| GB | 965010 | 7/1964 |
| GB | 1270410 | 4/1972 |
| GB | 2 073 024 | 10/1981 |
| GB | 2 140 684 | 12/1984 |
| HU | 9800078 A | 9/1999 |
| IT | 022309 | 12/1990 |
| JP | 60-21912 | 2/1985 |
| JP | SHO 58-126910 | 2/1985 |
| JP | 04244029 A | 9/1992 |
| JP | 11060493 | 3/1999 |
| JP | 11060493 A | 3/1999 |
| JP | 11 116488 A | 4/1999 |
| JP | 11116488 | 4/1999 |
| JP | 11 124335 A | 5/1999 |
| JP | 11124335 | 5/1999 |
| JP | 2000 327578 | 11/2000 |
| JP | 2000327578 | 11/2000 |
| WO | 87/07251 | 12/1987 |
| WO | WO 89/09054 | 10/1989 |
| WO | 92/13491 | 8/1992 |
| WO | 93/23092 | 11/1993 |
| WO | WO 93/23092 | 11/1993 |
| WO | 95/13704 | 5/1995 |
| WO | WO 95/13704 | 5/1995 |
| WO | 96/17595 | 6/1996 |
| WO | 98/41095 | 9/1998 |
| WO | WO 94/41095 | 9/1998 |
| WO | 98/51273 | 11/1998 |
| WO | 00/27390 | 5/2000 |
| WO | WO 00/27390 | 5/2000 |
| WO | 00/30697 | 6/2000 |
| WO | 00/44414 | 8/2000 |
| WO | 00/64505 | 11/2000 |
| WO | 00/64506 | 11/2000 |
| WO | 00/78282 | 12/2000 |
| WO | WO 0078281 | 12/2000 |
| WO | 01/15710 | 3/2001 |
| WO | 01/24839 | 4/2001 |
| WO | 01/26627 A1 | 4/2001 |
| WO | 01/27365 | 4/2001 |
| WO | 01/34686 | 5/2001 |
| WO | 01/41774 | 6/2001 |

| WO | 01/41819 | 6/2001 |
| WO | 01/43788 | 6/2001 |
| WO | 01/49115 | 7/2001 |
| WO | 01/49301 | 7/2001 |
| WO | 01/49301 A1 | 7/2001 |
| WO | 01/49302 | 7/2001 |
| WO | WO 01/49301 A1 | 7/2001 |
| WO | 01/68179 A1 | 9/2001 |
| WO | 01/70052 | 9/2001 |
| WO | 01/74300 | 10/2001 |
| WO | 01/80920 | 11/2001 |
| WO | 02/09729 | 2/2002 |
| WO | 02/15698 | 2/2002 |
| WO | WO 02/09729 A2 | 2/2002 |
| WO | 02/18003 | 3/2002 |
| WO | 02/18699 | 3/2002 |
| WO | 02/44625 | 6/2002 |

OTHER PUBLICATIONS

Djokic et al., "An Electrochemical Analysis of Thin Silver Films Produced by Reactive Sputtering", *Journal of the Electrochemical Society,* 148 (3) C191-C196 (2001).

Kirsner et al., The Role of Silver in Wound Healing: Part 3 "Matrix Metalloproteinases in Normal and Impaired Wound Healing: A Potential Role of Nanocrystalline Silver" *WOUNDS: A Compendium of Clinical Research and Practice* vol. 13, No. 3 May/Jun. 2001, Supplement C.

Olson, et al., "Healing of Porcine Donor Sites Covered with Silver-coated Dressings", *Eur J Surg* 2000; 166: 486-489.

Sant et al., "Novel duplex antimicrobial-silver films deposited by magnetron sputtering", *Philosophical Magazine Letters,* 2000, vol. 80, No. 4, 249-256.

Tredget, Metal Coated Dressing on a Porcine Wound "Evaluation of Wound Healing using Silver Dressing" Protocol No. 215/09/95 Feb. 22, 1996.

Tredget et al., "A Matched-Pair, Randomized Study Evaluating the Efficacy and Safety Acticoat Silver-Coated Dressing for the Treatment of Burn Wounds", *Journal of Burn Care & Rehabilitation* Nov./Dec. 1998.

Wright et al., "Early healing events in a porcine model of contaminated wounds: Effects of nanocrystalline silver on matrix metalloproteinases, cell apoptosis, and healing" *Wound Repair and Regeneration* May-Jun. 2002 0010308 May 15, 2002 14:24:35.

Wright et al., "The Comparative Efficacy of Two Antimicrobial Barrier Dressings: In-vitro Examination of Two Controlled Release of Silver Dressings" *WOUNDS: A Compendium of Clinical Research and Practice* vol. 10, No. 6, Nov./Dec. 1998.

Wright et al., "Wound management in an era of increasing bacterial antibiotic resistance: A role for topical silver treatment" *AJIC* vol. 26, No. 6.

Wright et al., "Efficacy of topical silver against fungal burn wound pathogens", *AJIC* vol. 27, No. 4.

Yin et al., "Comparative Evaluation of the Antimicrobial Activity of ACTICOAT Antimicrobial Barrier Dressing" *Journal of Burn Care & Rehabilitation* May/Jun. 1999.

Yin et al., "Effect of Acticoat Antimicrobial Barrier Dressing on Wound Healing and Graft Take", *Burn & Care Rehabilitation,* part 2, Jan./Feb. 1999.

Demling, et al., "The Role of Silver in Wound Healing: Effects of Silver on Wound Management," *Wounds,* vol. 13, No. 1, Jan./Feb. 2001 Supplement A; pp. 5-14.

Ovington, "The Role of Silver in Wound Healing: Why is Nanocrystalline Silver Superior? Nanocrystalline Silver: Where the Old and Familiar Meets a New Frontier," *Wounds,* vol. 13, No. 2, Mar./Apr. 2001, Supplement B; pp. 5-10.

Voigt, et al., "The Use of Acticoat as Silver Impregnated Telfa Dressings in a Regional Burn and Wound Care Center: The Clinicians View," *Wounds,* vol. 13, No. 2, Mar./Apr. 2001, Supplement B; pp. 11-20.

Shigemasa et al., "Applications of Chitin and Chitosan for Biomaterials" *Biotechnology & Genetic Engineering Reviews* vol. 13 (14) pp. 383-420.

Thornton, "Deposition Technologies for Films and Coatings: Coating Deposition By Sputtering" *Materials Science Series* 5 pp. 170-243 1982.

Thornton, "Influence of apparatus geometry and deposition conditions on the structure and topography of thick sputtered coatings" *J. Vac. Sci. Technol.,* vol. 11, No. 4, Jul./Aug. 1974.

Sant et al., "Morphology of Novel Antimicrobial Silver Films Deposited By Magnetron Sputtering" *Scripta Materiala,* vol. 41, No. 12, pp. 1333-1339, Nov. 19, 1999.

WPIDS abstract 1966-11488F (1966).

WPIDS abstract 1989-312257 (1989).

Medline abstract, accession No. 96064219 (1996).

Burrell et al., "Efficacy of Silver-Coated Dressings as Bacterial Barriers in a Rodent Burn Sepsis Model", *WOUNDS: A Compendium of Clinical Research and Practice* vol. 11, No. 4 Jul./Aug. 1999.

Demling, et al., "The Role of Silver in Wound Healing: Effects of Sliver on Wound Management," *Wounds,* vol. 13, No. 1, Jan./Feb. 2001 Supplement A; pp. 5-14.

Ovington, "The Role of Silver in Wound Healing: Why is Nanocrystalline Silver Superior? Nanocrystalline Silver: Where the Old and Familiar Meets a New Frontier," *Wounds,* vol. 13, No. 2, Mar./Apr. 2001, Supplement B; pp. 5-10.

Tredget et al., "A Matched-Pair, Randomized Study Evaluating the Efficacy and Safety Acticoat* Silver-Coated Dressing for the Treatment of Burn Wounds", *Journal of Burn Care & Rehabilitation* Nov./Dec. 1998; 19:531-7.

Voigt, et al., "The Use of Acticoat as Silver Impregnated Telfa Dressings in a Regional Burn and Wound Care Center: The Clinicians View," *Wounds,* vol. 13, No. 2, Mar./Apr. 2001, Supplement B; pp. 11-20.

Wright et al., "Early healing events in a porcine model of contaminated wounds: effects of nanocrystalline silver on matrix metalloproteinases, cell apoptosis, and healing" *Wound Repair and Regeneration* 2002; 10:141-151.

Wright et al., "The Comparative Efficacy of Two Antimicrobial Barrier Dressings: In-vitro Examination of Two Controlled Release of Silver Dressings" *Wounds* vol. 10, No. 6, Nov./Dec. 1998, pp. 179-188.

Wright et al., "Efficacy of topical silver aginst fungal burn wound pathogens", *AJIC* vol. 27, No. 4, Aug. 1999.

Wright et al., "Wound Management in an era of increasing bacterial antibiotic resistance: A role for topical silver treatment" *AJIC* vol. 26, No. 6; pp. 572-577 Dec. 1998.

Yin et al., "Comparative Evaluation of the Antimicrobial Activity of ACTICOAT* Antimicrobial Barrier Dressing" *Journal of Burn Care & Rehabilitation,* vol. 20, No. 3 May/Jun. 1999.

Yin et al., "Effect of Acticoat Antimicrobial Barrier Dressing on Wound Healing and Graft Take", *Burn Care & Rehabilitation,* part 2, Jan./Feb. 1999.

* cited by examiner

TRANSCUTANEOUS MEDICAL DEVICE DRESSINGS AND METHOD OF USE

FIELD OF THE INVENTION

The invention relates to transcutaneous medical device dressings, and processes for their production and use, for controlling infections.

BACKGROUND OF THE INVENTION

Transcutaneous medical devices are catheters, pins, implants and the like which pass through the skin and are indwelling for some considerable time. Exemplary of transcutaneous medical devices are central venous catheters, peripheral venous catheters, Swan-Gaus pulmonary catheters, central nervous system implants (ex. external ventricular drainage and ventricular reservoirs), peritoneal dialysis catheters, such as for continuous ambulatory peritoneal dialysis and continuous cyclic peritoneal dialysis, hemodialysis catheters, transvenous pacemaker leads and temporary orthopedic pins. All of these transcutaneous medical devices, when in place, have a portion of the device which is external, that is which is left protruding from the skin, and which can be the cause of infection.

The risk of acquiring infections from transcutaneous infections is very high. For instance, the risk of acquiring catheter-related bloodstream infection ranges from 0.9 to 8%. This nosocomial bloodstream infections cause a case fatality of more than 20%, and account for an increase of thousands of dollars in hospital costs per infection, or tens of thousands of dollars per survivor in ICU needing an extra week of hospital stay. As for peritoneal dialysis, a very experienced center today still has a peritonitis rate of one episode per 15 to 25 patient months. The major sources of bacteria in these infections are from surrounding skin.

To prevent infections associated with transcutaneous medical devices antiseptic preparation of insertion sites, including the initial application of topical anti-microbial solutions such as alcohol or iodine to the insertion sites is known. A further topical ointment after insertion of the device, such as an ointment containing neomycin, polymyxin and bactracin, has been shown to prevent catheter colonization/infection, but it may increase the risk of fungal infection. Ointments are also inconvenient, requiring multiple replacements. There have also been attempts to attach a cuff to the catheters, with an anti-microbial agent impregnated in the cuff. Efforts to coat the catheters with anti-microbial agents are known. However, none of these efforts has been completely successful in clinical trials. Presently, the most common catheter dressing used in hospitals comprises sterile gauze or polyurethane film, which have limited infection control properties.

Recent efforts to replace gauze with a transparent film dressing to allow a visual check on the insertion site is known, see for instance U.S. Pat. No. 5,372,589, issued Dec. 13, 1994 to Davis. No anti-microbial control is taught with such a dressing. Johnson & Johnson Medical Inc. markets a product under the trade mark BIOPATCH, which is a chlorhexidine gluconate-impregnated catheter patch. An Iodophor transparent dressing has also been suggested. However, to date, no completely effective anti-microbial device for use with transcutaneous medical devices is known.

A securement device is taught for securing an intravenous device to the body in U.S. Pat. No. 3,918,446, issued Nov. 11, 1975 to Buttaravoli. The device has an upper and a lower pad, between which the intravenous device is fixed. Since the function of the device is to secure the device to the body, there is a teaching to provide an adhesive material to the bottom of lower pad, and to the bottom of the top pad. There is a mention of providing the adhesive with an antibacterial agent. This device has the disadvantage of using adhesives with the antibacterial agent, which limits the effectiveness and long lasting ability of the antibacterial agent. Furthermore, the adhesive can be irritating next to the skin, cause skin damage and patient discomfort on removal, and inhibits the removal or changing of the device. Furthermore, many adhesives act as moisture barriers, which can limit the effectiveness of the antibacterial agent. Finally, the device of this patent teaches including a slit in the bottom pad of the dressing, which lies below the intravenous needle or catheter when the device is in place, allowing the intravenous device to remain in contact with the skin, and therefore limiting the infection control of the device.

SUMMARY OF THE INVENTION

In one broad aspect, the invention provides a transcutaneous device dressing for use with a transcutaneous medical device which has punctured the skin of a patient and which has a portion of the medical device protruding from the skin, comprising:

a top and a bottom dressing, both being formed from a flexible material and having upper and lower surfaces, with the lower surface being skin facing in use;

the bottom dressing having a slit formed therein extending from one edge inwardly to a termination point within the confines of the bottom dressing;

an anti-microbial material provided without adhesives at the upper and lower surfaces of the bottom dressing, and at least at the lower surface of the top dressing;

whereby, in use, the bottom dressing is placed next to the skin, the slit allowing the bottom dressing to surround the puncture site such that the lower surface of the bottom dressing is in contact with the skin and the upper surface of the bottom dressing is in contact with a portion of the medical device protruding from the skin, and the top dressing is placed above the puncture site such that its lower surface is in contact with a portion of the medical device protruding from the skin, thereby exposing a portion of the medical device protruding from the skin from above and below to the anti-microbial activity of the anti-microbial material.

In another broad aspect, the invention provides a method of dressing the puncture site of a transcutaneous medical device to limit infection by microorganisms from the surrounding skin and the portion of the medical device that protrudes from the skin of a patient, comprising:

providing a transcutaneous device dressing, comprising:

a top and a bottom dressing, both being formed from a flexible material and having upper and lower surfaces, the lower surfaces being skin facing when the dressing is in use, the bottom dressing having a slit formed therein extending from one edge inwardly to a termination point within the confines of the bottom dressing; and an anti-microbial material provided without the use of adhesives at the upper and lower surfaces of the bottom dressing, and at least at the lower surface of the top dressing;

sliding the bottom dressing in place next to the skin using the slit to allow the bottom dressing to surround the puncture site at the termination point such that the lower surface of the bottom dressing is in contact with the skin surrounding the puncture site while the upper surface of the bottom dressing is in contact with a portion of the medical device protruding from the skin;

applying the top dressing above bottom dressing such that its lower surface is in contact with a portion of the medical device protruding from the skin;

depending on the anti-microbial material, applying a water or alcohol based electrolyte to the top and bottom dressings to release the anti-microbial agent; and fixing the top and bottom dressings to the skin, preferably with an occlusive or semi-occlusive layer such as an adhesive film.

The transcutaneous device dressing of this invention has the advantage of ease of placement and been demonstrated to be much more effective than disc type dressings which are laid flat under the transcutaneous device, which have only a limited portion, generally only the thickness of the dressing (less than 3 mm), in contact with the portion of the medical device which protrudes from the skin.

Preferably, the dressing of this invention is formed such that the top and bottom dressings are joined along a fold line, that is they are formed from a unitary dressing which is folded over in use. The slit is preferably formed from the edge of the bottom dressing which is parallel to the fold. The dressing is preferably formed from multilayered, laminated dressing materials. The anti-microbial material is preferably a thin film of an anti-microbial metal, most preferably formed with atomic disorder so as to create an effective anti-microbial effect, and to create an interference colour so as to provide an indicator, as described in WO98/41095, published Sep. 24, 1998, and naming inventors R. E. Burrell and R. J. Precht.

The dressing of this invention has application to transcutaneous medical devices such as listed above, made from a wide variety of materials, for example metals, including steel, aluminum and its alloys, latex, nylon, silicone, polyester, polyurethane, and other plastics and rubbers. Such devices are generally made of a bioinert or Biocompatible material. The device may take a variety of shapes including rod or tube shapes, hollow or solid, and may be rigid or flexible, factors dictated by its intended utility.

As used herein and in the claims, the terms and phrases set out below have the meanings which follow.

"Metal" or "metals" includes one or more metals whether in the form of substantially pure metals, alloys or compounds such as oxides, nitrides, borides, sulphides, halides or hydrides.

"Anti-microbial metals" are metals whose ions have an anti-microbial effect. Preferably, the metal will also be biocompatible. Preferred anti-microbial metals include Ag, Au, Pt, Pd, Ir (i.e. the noble metals), Sn, Cu, Sb, Bi and Zn, with Ag being most preferred.

"Biocompatible" means non-toxic for the intended utility. Thus, for human utility, biocompatible means non-toxic to humans or human tissues.

"Anti-microbial effect" means that atoms, ions, molecules or clusters of the anti-microbial metal (hereinafter "species" of the anti-microbial metal) are released into the alcohol or electrolyte which the material contacts in concentrations sufficient to inhibit bacterial (or other microbial) growth in the vicinity of the material. The most common method of measuring anti-microbial effect is by measuring the zone of inhibition (ZOI) created when the material is placed on a bacterial lawn. A relatively small or no ZOI (ex. less than 1 mm) indicates a non useful anti-microbial effect, while a larger ZOI (ex. greater than 5 mm) indicates a highly useful anti-microbial effect. One procedure for a ZOI test is set out in the Examples which follow.

"Sustained release" or "sustainable basis" are used to define release of atoms, molecules, ions or clusters of an anti-microbial metal that continues over time measured in hours or days, and thus distinguishes release of such metal species from the bulk metal, which release such species at a rate and concentration which is too low to achieve an anti-microbial effect, and from highly soluble salts of anti-microbial metals such as silver nitrate, which releases silver ions virtually instantly, but not continuously, in contact with an alcohol or electrolyte.

"Atomic disorder" includes high concentrations of: point defects in a crystal lattice, vacancies, line defects such as dislocations, interstitial atoms, amorphous regions, gain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e. which freeze-in atomic disorder, means diffusion of atoms and/or molecules on the surface or in the matrix of the material being formed.

"Alcohol or water-based electrolyte" is meant to include any alcohol or water-based electrolyte that the anti-microbial materials of the present invention might contact in order to activate (i.e., cause the release of species of the anti-microbial metal) into same. The term is meant to include alcohols, water, gels, fluids, solvents, and tissues containing water, including body fluids (for example blood, urine or saliva), and body tissue (for example skin, muscle or bone).

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the anti-microbial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

DESCRIPTION OF THE PREFERRED EMBODIMENTS

Transcutaneous Device Dressing

Figure 1:
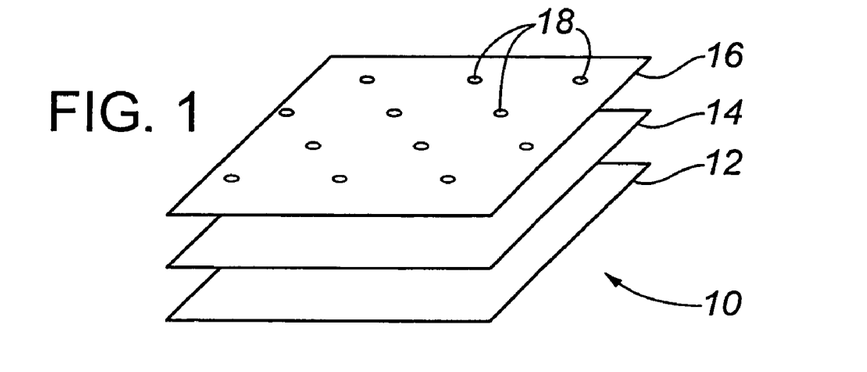
FIG. 1 is a schematic sectional figure of a three layer transcutaneous device dressing in accordance with the present invention.

The dressing in accordance with the invention includes at least one, and preferably at least two or three layers of medical dressing materials, laminated together by known means such as low temperature thermal fusing, stitching or, most preferably, ultrasonic welding. A three layer dressing in accordance with the invention is shown generally at 10 in FIG. 1 to include a first layer 12, which will be skin facing in use, a second layer 14, which preferably forms an absorbent core, and a third layer 16. The layers 12, 14 and 16 are shown to be laminated together by ultrasonic welds 18 at intermittent locations across the dressing 10.

Figure 2:
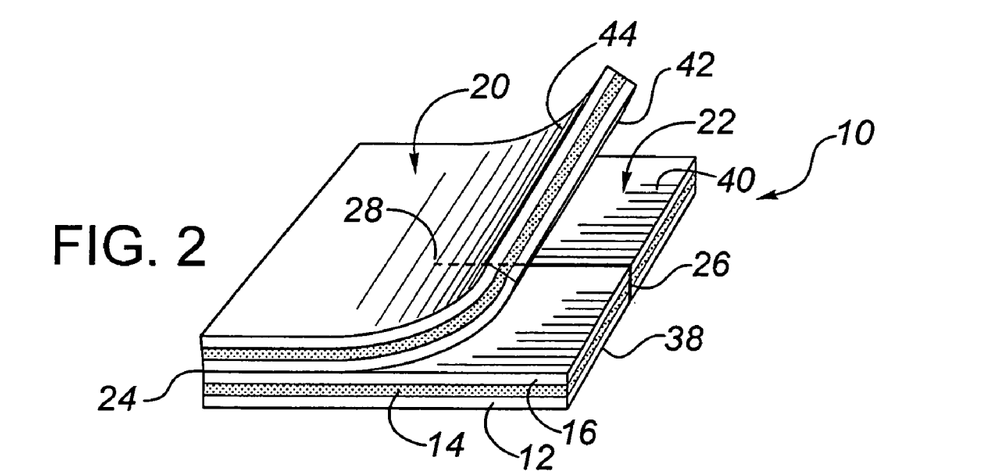
FIG. 2 is a schematic perspective view of a three layer transcutaneous device dressing folded along a central line to form top and bottom dressings and showing the slit for placement around the transcutaneous medical device.

FIG. 2 shows the dressing 10 to comprise a top dressing 20 and a bottom dressing 22 formed from the three layers 12, 14 and 16. In FIG. 2, the top and bottom dressings 20, 22 are joined along a fold line 24, being formed from a unitary dressing 10. However, in accordance with this invention, the top and bottom dressings 20, 22 may be formed from separately, from same or different medical dressing materials. If the top and bottom dressings 20, 22 are provided separately, the top dressing 20 may include an occlusive or semi-occlusive layer such as an adhesive film (not shown) in order to secure the dressing 10 in place, and retain moisture for activation of the anti-microbial material. A slit 26 is formed in the bottom dressing 22, preferably extending from the edge of the bottom dressing 22 which is parallel to the fold line 24, and terminating at a termination point 28 which is preferably about the center point of the bottom dressing 22.

Figure 3:
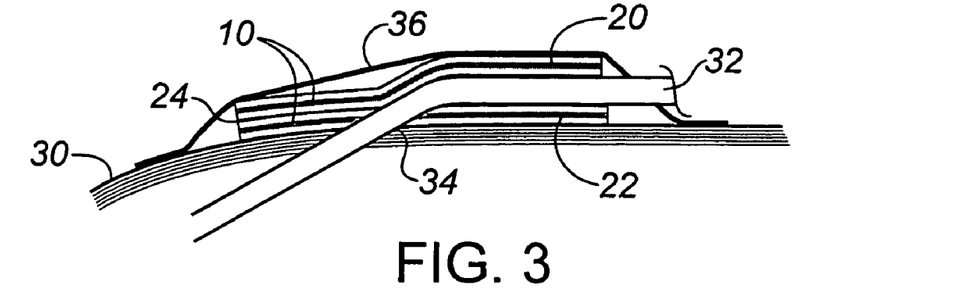
FIG. 3 is a schematic sectional view of the folded transcutaneous device dressing in place with a catheter penetrating the skin of a patient.

The dressing 10 is shown in place against the skin 30 of a patient in FIG. 3, with a catheter 32 protruding from the skin 30 at a penetration site 34. The dressing is held in place against the skin with an occlusive or semi-occlusive layer 36, such as adhesive tape or polyurethane film. The dressing is sized to cover a significant portion of the catheter 32 that protrudes from the skin 30, and not just the immediate skin area surrounding the penetration site. This aids in limiting infection, since bacteria are prevented from migrating along the catheter 32. A minimum dressing size will preferably provide at least 5 mm coverage of the protruding catheter 32, more preferably 1–5 cm coverage.

Depending on the size of the transcutaneous medical device, the termination point 28 of the slit 26, may include additional cuts, preferably a cross-cut, or a penetrating hole (not shown), to allow the medical device to fit through the dressing, while still maintaining the portions around the termination point in close contact with both the skin and protruding section of the medical device.

Figure 4:
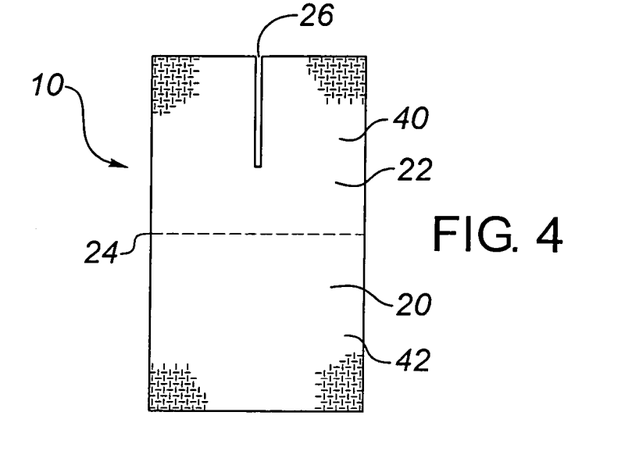
FIG. 4 is a plan view of the transcutaneous device dressing of this invention, showing the slit in the bottom dressing.
Figure 5:
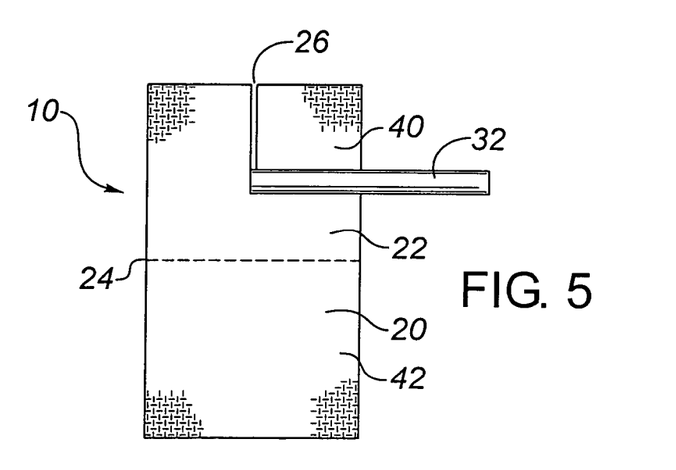
FIG. 5 is a plan view of the transcutaneous device dressing slid in place with a catheter, such that the bottom dressing is in contact with a portion of the catheter protruding from the skin.
Figure 6:
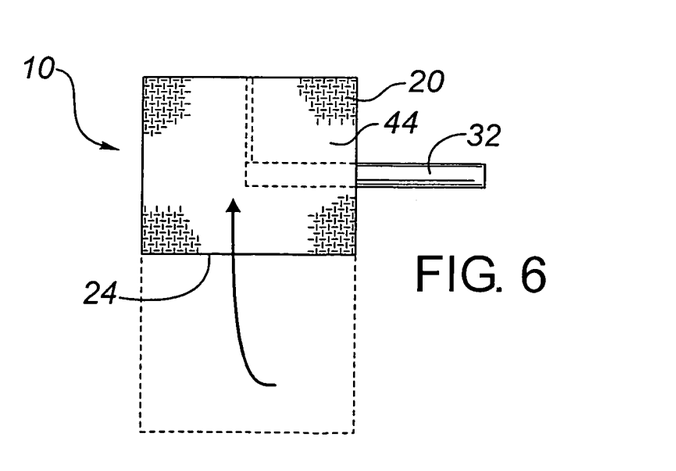
FIG. 6 is a plan view of transcutaneous device dressing folded such that the top dressing is in contact with a portion of the catheter protruding from the skin.

FIGS. 4, 5, and 6 demonstrate placement of the dressing 10 around a catheter 32, with the bottom dressing 22 sliding under the catheter 32 such that the lower surface 38 (see FIG. 2) of the bottom dressing 22 contacts the patient's skin (not shown), while the upper surface 40 of the bottom dressing 22 contacts the catheter 32 protruding from the skin. Once the top dressing 20 is applied, by folding it over the bottom dressing 22, the lower surface 42 (see FIG. 2) of the top dressing 20 is in contact with the catheter 32 protruding from the skin. The upper surface 44 of the top dressing 20 is then covered with the occlusive or semi-occlusive layer 36, as shown in FIG. 3. As shown in FIGS. 4 and 5, when the dressing 10 is formed from a unitary dressing, the lower surface 42 of the top dressing 20 and the upper surface 40 of the bottom dressing 22, are one and the same layer, represented as layer 16 in FIG. 1.

The lower and upper surfaces 38 and 40 of the bottom dressing 22, and at least the lower surface 42 of the top dressing 20 are provided with an anti-microbial material in order to limit infection. Anti-microbial materials for use with medical dressing materials are well known in the art. The anti-microbial material may be impregnated in one or more of the layers of the dressing 10, but will more preferably be provided as a thin film of an anti-microbial metal on those surfaces of the top and bottom dressings 20, 22 which will be skin or catheter facing once the dressing is in place. Alternatively, the anti-microbial material may be an antibiotic composition or a composition formed from an anti-microbial metal, as are well known in the art.

The preferred and alternate compositions of the layers 12, 14 and 16, together with the preferred anti-microbial metal coatings are set out in further detail below.

Dressing Materials

The first layer 12 of the dressing 10 is formed of a perforated, preferably non-adherent material which allows for fluids to penetrate or diffuse there through in either or both directions. The perforated material may be formed of a woven or non-woven, non-woven being preferred, fabric such as cotton, gauze, a polymeric net or mesh such as polyethylene, nylon, polypropylene or polyester, an elastomer such as polyurethane or polybutadiene elastomers, or a foam such as open cell polyurethane foam. Exemplary perforated, non-adherent materials useful for the dressing include non-woven meshes such as; DELNET™ P530, which is a non-woven veil formed of high density polyethylene using extrusion, embossing and orientation processes, produced by Applied Extrusion Technologies, Inc. Of Middletown, Del., USA. This same product is available as Exu-Dry CONFORMANT 2™ Wound Veil, from Frass Survival Systems. Inc., Bronx, N.Y., USA as a subset of that company's Wound Dressing Roll (Non-Adherent) products. Other useful non-woven meshes include CARELLE™ or NYLON 90™ available from Carolina Formed Fabrics Corp., N-TERFACE™ available from Winfield Laboratories, Inc., of Richardson, Tex., USA. Exemplary woven meshes may be formed from fiberglass or acetate, or cotton gauze. An exemplary hydrophilic polyurethane foam is HYPOL™ available from W. R. Grace & Co., New York, N.Y., USA For ease of ultrasonic welding for lamination, at least one of the first and second layers 12, 14 is preferably formed from a polymeric material which is amenable to ultrasonic welding, that is which will melt on the application of localized heat and then fuse the layers together on cooling.

The second, absorbent layer 14 is formed from an absorbent material for holding sufficient moisture next to the skin in order to activate the anti-microbial metal coating, that is to cause release of ions, molecules, atoms or clusters of the anti-microbial metal in order to cause an anti-microbial effect. Preferably, the absorbent material is an absorbent needle punched non-woven rayon/polyester core such as SONTARA™ 8411, a 70/30 rayon/polyester blend commercially available from Dupont Canada, Mississauga, Ontario, Canada. This product is sold by National Patent Medical as an American White Cross sterile gauze pad. However, other suitable absorbent materials include woven or non-woven materials, non-woven being preferred made from fibers such as rayon, polyester, rayon/polyester, polyester/cotton, cotton and cellulosic fibers. Exemplary are creped cellulose wadding, an air felt of air laid pulp fibers, cotton, gauze, and other well known absorbent materials suitable for medical dressings.

The third layer 16 of the dressing 10 is preferably formed of perforated, non-adherent material such as used in the first layer 12. This allows moisture penetration as sterile water and the like are added in order to activate the anti-microbial metal coating.

Additional layers (not shown) may be included between or above the first, second and third layers 12, 24, 16, as is well known in medical. Thus the use of the terms first, second and third layer, as used herein and in the claims is not meant to exclude such additional layers.

The layers 12, 14, and 16 laminated together at intermittent spaced locations across the dressing 10 by ultrasonic welds 18. Ultrasonic welding is a known technique in the quilting art, and thus will not be discussed at length. Briefly, heat (generated ultrasonically) and pressure are applied to either side of the dressing 10 at localized spots through an ultrasonic horn so as to cause melting of at least one of the plastic materials in the first and second layers 12, 14, and the subsequent bonding together of the layers on cooling. The welds appear at localized circular spots and are preferably less than 0.5 cm in diameter. If the third layer 16 is present, the ultrasonic welding can be performed from either side of the dressing, and will bind all three layers 12, 14 and 16 together.

The use of ultrasonic welding of the layers at spaced locations has the advantage of retaining the absorbent and moisture penetration properties of the layers 12, 14, while retaining the conforming properties of the dressing. Edge seams, stitching and adhesives have the disadvantage of interfering with one or more of these desirable properties of the dressings. Furthermore, by spacing the welds 18 at intermittent locations across the dressing, the dressing 10 may be cut to smaller sizes, as needed, without causing delamination. Preferred spacings of about 2.5 cm between welds allows the dressing to be cut down to about 2.5 cm sizes, while maintaining at least one weld to hold the laminated layers together.

Anti-Microbial Coating

The dressing 10 of this invention preferably includes an anti-microbial coating formed from an anti-microbial metal.

The coating is applied to one or more of the layers 12, 14, 16, but is most preferably applied at least to the first and third layers 12 and 16, so as to provide the anti-microbial effect both against the skin and against the transcutaneous medical device held between the top and bottom dressings 20, 22.

The coating is most preferably formed with atomic disorder in accordance with the procedures set out above and as described in U.S. Pat. No. 5,454,886, and WO98/41095, both to Burrell et al. Most preferably, the coating is formed as a multilayer anti-microbial coating having a top and a base layer, as set below, to produce an interference colour. In this way, the coating provides not only an anti-microbial effect to limit infection, but also acts as an indicator of activation of the dressing. As the top layer of the coating is activated with an alcohol or water-based electrolyte, such as sterile water or ethanol, even minor dissolution of the anti-microbial metal results in a detectable colour change, indicating that an anti-microbial effect is being provided. If there is no colour change, additional moisture might be provided to the dressing by adding water, until a colour change is detected. Once activated, the dressing should be maintained in a moist condition by the addition of sterile water if necessary.

Sterilization

Dressings 10 with anti-microbial coatings of an anti-microbial metal formed with atomic disorder are preferably sterilized without applying excessive thermal energy, which can anneal out the atomic disorder, thereby reducing or eliminating a useful anti-microbial effect. Gamma radiation is preferred for sterilizing such dressings, as discussed in U.S. Pat. No. 5,454,886.

It should be appreciated that the use of ultrasonic welding to laminate the layers of dressings with anti-microbial coatings formed from anti-microbial metals with atomic disorder is advantageous since it achieves bonding in localized spots and avoids applying heat to any significant portion of the dressing, thereby avoiding any significant reduction in the anti-microbial effect through annealing out of atomic disorder.

The sterilized dressings should be sealed in packaging which excludes light penetration to avoid additional oxidation of the anti-microbial coating. Polyester peelable pouches are preferred. The shelf life of anti-microbial dressings thus sealed is over one year.

Directions for Use of Dressings with Transcutaneous Devices

With transcutaneous devices such as flexible catheters, the dressing 10 is placed on the skin around the catheter 32 by passing the catheter 32 through the slit 26. The dressing 10 is rotated, if needed, to ensure that slit 26 is roughly perpendicular to the long axis of the catheter 32, thus ensuring that the portion of the catheter 32 protruding from the skin is contacted by the upper surface 40 of the bottom dressing 22. The top dressing 20 is folded over the bottom dressing 22 (or placed over, if the top and bottom dressings are separate), such that the lower surface 42 of the top dressing 20 is in contact with the portion of the catheter 32 protruding from the skin. If the anti-microbial material is an anti-microbial metal coating, the dressing is then moistened with drops of sterile water or 70% ethanol, in order to activate the coating for release of anti-microbial metal species. The dressing 10 is then secured in place with an occlusive or semi-occlusive layer 36, such as an adhesive film, which keeps the dressing in a moist environment.

If the transcutaneous device is rigid, such as a temporary orthopedic pin, the bottom dressing 22 is put in place as set out above, but the top dressing 20 is then folded and secured around the portion of the pin protruding from the skin, in a tent-like manner, since the pin generally protrudes at an angle normal to the skin surface.

Animal trials with the dressing of the present invention, carrying a bi-layer anti-microbial coating formed with silver having atomic disorder, manufactured as set out above and as described in greater detail in Example 3, have shown excellent results in controlling infection. In use, the dressings are kept moist, at 100% relative humidity. Adding sterile water initially to activate the anti-microbial metal coating is needed, and then as needed to maintain the dressing in a moist condition. Dressings may be changed as required for observation and cleaning, but need not be changed more frequently than every 7 days, and can provide an anti-microbial effect for a much longer period of time.

Multilayer Anti-Microbial Materials With Interference Colour

The dressings preferably include the anti-microbial metal coating formed with at least two metal layers, a base layer and a top layer over the base layer, so as to produce an interference colour, as set forth in WO98/41095. Both layers are partly reflective; the top layer is partly light transmissive. The top layer is a thin film containing at least one anti-microbial metal formed with sufficient atomic disorder such that the top layer, in contact with an alcohol or water based electrolyte, releases ions, atoms, molecules or clusters of the anti-microbial metal at a concentration sufficient to provide a localized anti-microbial effect on a sustainable basis. In this way, the top layer, in contact with the alcohol or electrolyte, will undergo a change in optical path length, either by a change in thickness resulting from some dissolution, or through a change in the refractive index of the top layer resulting from a change in the composition of a newly formed thin layer formed on the top layer. Either or both of these results are sufficient to cause a detectable colour change, thus providing an indicator that the top layer has been activated.

Both the base layer and the top layer are formed from a partly reflective material. In this way, at least a portion of the incoming light is reflected from the surface of the layer while another portion is transmitted through the layer. The top layer is partly light transmissive to allow incident light to reach the interface with the base layer. The top layer thus cannot approximate 100% reflectivity, such as in pure Al or Ag, or interference colours cannot be generated, as is well known in the art. The materials for the top and base layers should be balanced in their reflectances in order to generate an interference colour. Generally, the top layer is deposited as a thin film having a thickness which maintains adequate transmittance to generate an interference colour. Furthermore, the refractive index for the materials in layers is different, accomplished by differences in their actual or effective compositions. For instance different materials in the two layers will result in the materials having different actual refractive indexes. However, if it is desired to make the layers from the same material, the layers can be deposited with different porosities or different levels/types of atomic disorder, in order to achieve different effective compositions, and thus different refractive indexes.

In this manner, incoming light reflects off the interface of the base and top layers. Incoming light reflects from the interface of the top layer with air, and interferes with the light reflected from the interface with the base layer so as to generate an "interference colour". The particular colour which is generated and its brightness will depend on the properties of the layers, most importantly on the composition of the layers, which determines its transmittance and absorption properties, along with its refractive index, and on the thickness of the layers. Generally, it is desirable to generate first and second order interference colours, by limiting the thickness of the base layer and top layers to minimize the number of internal reflections. First and second order interference colours are generally brighter than third and fourth order etc. colours, making them more aesthetically pleasing, more consistently reproducible in manufacturing, and more susceptible to detectable colour change on variations in thickness on dissolution of even a minor amount of the top layer.

The property which determines the particular colour which is generated is the effective optical thickness of the top layer, that is the product of the refractive index of the top layer material and the actual thickness of the top layer. Thus the colour which is desired can be altered by changing the actual thickness or the top layer or its refractive index.

Preferably, the material in the base layer is a reflective metal. Such metals are known in the art and include, for example one or more of the valve metals, e.g., Ta, Nb, Ti, Zr and Hf, as well as transition metals such as Au, Ag, Pt, Pd, Sn, Cu, V, W and Mo, or the metal Al. More preferably, the base material is formed from Ag, Au, Pt, Pd, Cu, Ta and Al. Use of a metal such as tantalum as the base layer may cause reduction of oxide containing materials in the top layer. To avoid this, a barrier layer (not shown), such as tantalum oxide formed by anodizing at least a portion of the top surface of the Ta metal, should be included above a tantalum layer. Preferred metals for the base layer are the anti-microbial metals Au, Ag, Pt, Pd, Sn and Cu, more preferably Au, Pt and Ag, and most preferably Ag, in a partly reflective form.

The base layer may be formed by known techniques, such as the vapour deposition techniques of evaporation or physical vapour deposition. Preferably, the base layer is formed as a thin film by physical vapour deposition with atomic disorder, as set out below and in U.S. Pat. No. 5,454,889, in order to produce a sustainable anti-microbial effect when the base layer is ultimately exposed to an alcohol or water based electrolyte. The thickness of the base layer is generally not critical, provided that it is partly reflective. Preferred thicknesses will vary widely with the material composition and the desired colour. However, in that the layer is preferably a thin film formed by physical vapour deposition techniques, it should be at least about 25 nm thick to create a useful colour. To generate first and second order interference colours and to produce an anti-microbial effect, the base layer should be greater than 60 nm thick, more preferably 300 to 2500 nm thick, and most preferably 600 to 900 nm thick.

The top layer is formed of a partly reflective, partly light transmissive thin film containing at least one anti-microbial metal formed with atomic disorder so as to produce a sustainable anti-microbial effect, and ultimate colour change, when exposed to an alcohol or a water based electrolyte. The anti-microbial metal is preferably one or more of Ag, Au, Pt, Pd, Ir, Sn, Cu, Sb, Bi, and Zn in a partly reflective, partly transmissive form. More preferably, the anti-microbial metal is Ag, Au, Pt, Pd or Cu. The thickness of the top layer formed from these metals is preferably less than 400 nm in order to maintain the preferred level of light transmission. The desired thickness will vary with the composition of the top layer, and with the desired end colour and colour change. For first and second order interference colours, the thickness will generally be less than about 400 nm. More preferably, the thickness will range from 5 to 210 nm, most preferably from 10 to 100 nm.

The top layer may be a thin film of the base layer material, formed with a different refractive index for instance by altering the deposition conditions to change the porosity, composition and/or degree of atomic disorder in the layers.

When the base layer is itself formed from an anti-microbial metal with atomic disorder, the top layer may be provided as an in situ generated top layer by virtue of its thickness and/or composition changing on contacting an alcohol or water based electrolyte, so as to produce an interference colour which differs from the initial colour of the base layer.

Most preferably, the top layer is a thin film of a composite material formed by co-, sequentially or reactively depositing an anti-microbial metal in a matrix with atoms or molecules of a different material to create atomic disorder in the matrix, in the manner set out below. The different material is selected from a) biocompatible metals, b) oxygen, nitrogen, hydrogen, boron, sulphur or halogens, or c) an oxide, nitride, carbide, boride, halide, sulphide or hydride of either or both of an anti-microbial metal or a biocompatible metal. Most preferably, the top layer material is a composite material containing silver, and one or both of silver oxide and atoms or molecules containing oxygen trapped or absorbed in the sliver matrix. The term "silver oxide" is meant to include any oxide or mixture of oxides of silver. However, the top layer is preferably not formed solely of AgO and/or $Ag_2O$, since the solubility of these materials is low for providing a useful anti-microbial effect.

Anti-Microbial Materials Containing Atomic Disorder

At least the top layer, and preferably also the base layer, is formed in a crystalline form from anti-microbial metals with atomic disorder so as to produce an anti-microbial effect. The production of atomic disorder through physical vapour deposition techniques is described in U.S. Pat. No. 5,454,886, and as outlined below.

The anti-microbial metal is deposited as a thin metallic film on one or more surfaces of the dressing 10, by vapour deposition techniques. Physical vapour techniques, which are well known in the art, all deposit the metal from the vapour, generally atom by atom, onto a substrate surface. The techniques include vacuum or arc evaporation, puttering, magnetron sputtering and ion plating. The deposition is conducted in a manner to create atomic disorder in the coating as defined above. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, supra). While such conditions have been investigated in the art, they had not been linked to enhanced solubility of the coatings so-produced prior to Applicants inventions.

The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3, and optionally one or both of:

a higher than normal working (or ambient) gas pressure, i.e. for vacuum evaporation: e-beam or arc evaporation, greater than 0.01 mT, gas scattering evaporation (pressure plating) or reactive arc evaporation, greater than 20 mT; for sputtering: greater than 75 mT; for magnetron sputtering: greater than about 10 mT; and for ion plating: greater than about 200 mT; and maintaining the angle of incidence of the coating flux on the surface to be coated at less than about 75', and preferably less than about 30°.

The metals used in the coating are those known to release ions etc. having an anti-microbial effect, as set out above. For most dressings, the metal must also be biocompatible. Preferred metals include the noble metals Ag, Au, Pt, Pd, and Ir as well as Sn, Cu, Sb, Bi, and Zn or alloys or compounds of these metals or other metals. Most preferred is Ag or Au, or alloys or compounds of one or more of these metals.

For economic reasons, the thin metal film has a thickness no greater than that needed to provide release of metal ions on a sustainable basis over a suitable period of time, and to generate the desired interference colour. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The anti-microbial effect of the material so produced is achieved when the coating is brought into contact with an alcohol or a water based electrolyte, thus releasing metal ions, atoms, molecules or clusters. The concentration of the metal species which is needed to produce an anti-microbial effect will vary from metal to metal. Generally, anti-microbial effect is achieved in body fluids such as plasma, serum or urine at concentrations less than about 0.5–5 µg/ml.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at $T/Tm<0.5$ and a working gas pressure of about 7 mTorr releases approximately ⅓ of the silver ions that a film deposited under similar conditions, but at 30 mTorr, will release over 10 days. Films that are created with an intermediate structure (ex. lower pressure, lower angle of incidence etc.) have Ag release values intermediate to these values as determined by bioassays. This then provides a method for producing controlled release metallic coatings. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 15 mTorr) for 50% of the deposition time and high (ex. 30 mTorr) for the remaining time, has a rapid initial release of metal ions, followed by a longer period of slow release. This type of coating is extremely effective on devices such as urinary catheters for which an initial rapid release is required to achieve immediate anti-microbial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable $\Delta T$, that the temperature differential between the substrate temperature during deposition and the ultimate temperature of use, will vary from metal to metal. For the most preferred metals of Ag and Au, preferred substrate temperatures of –20 to 200° C., more preferably –10° C. to 100° C. are used.

Atomic order may also be achieved, in either or both of the base and top layers by preparing composite metal materials, that is materials which contain one or more anti-microbial metals in a metal matrix which includes atoms or molecules different from the anti-microbial metals.

The preferred technique for preparing a composite material is to co- or sequentially deposit the anti-microbial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the anti-microbial metals, which results in atomic disorder during deposition. Alloys of this kind can also serve to reduce atomic diffusion and thus stabilize the disordered structure. Thin film deposition equipment with multiple targets for the placement of each of the anti-microbial and inert metals is preferably utilized. When layers are sequentially deposited the layer(s) of the inert metal(s) should be discontinuous, for example as islands within the anti-microbial metal matrix. The final ratio of the anti-microbial metal(s) to inert metal(s) should be greater than about 0.2. The most preferable inert metals are Ti, Ta, Zn and Nb. It is also possible to form the anti-microbial coating from oxides, carbides, nitrides, sulphides, borides, halides or hydrides of one or more of the anti-microbial metals and/or one or more of the inert metals to achieve the desired atomic disorder.

Another composite material may be formed by reactively co- or sequentially depositing, by physical vapour techniques, a reacted material into the thin film of the anti-microbial metal(s). The reacted material is an oxide, nitride, carbide, boride, sulphide, As hydride or halide of the anti-microbial and/or inert metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final ratio of anti-microbial metal(s) to reaction product should be greater than about 0.2. Air, oxygen, nitrogen and hydrogen are particularly preferred reactants.

The above deposition techniques to prepare composite coatings may be used with or without the conditions of lower substrate temperatures, high working gas pressures and low angles of incidence previously discussed. One or more of these conditions are preferred to retain and enhance the amount of atomic disorder created in the coating.

EXAMPLES

Example 1

This example shows the preparation of a bilayer anti-microbial silver coating on a dressing material. A high density polyethylene dressing, DELNET™ or CONFORMANT 2™ was coated with a silver base layer and a silver/oxide top layer to generate a coloured anti-microbial coating having indicator value. The coating layers were formed by magnetron sputtering under the conditions set out in Table 1.

TABLE 1

| Sputtering Conditions: | Base Layer | Top Layer |
| --- | --- | --- |
| Target | 99.99% Ag | 99.99% Ag |
| Target Size | 20.3 cm diameter | 20.3 cm diameter |
| Working Gas | 96/4 wt % Ar/O$_2$ | 96/4 wt % Ar/O$_2$ |
| Working Gas Pressure | 40 mTorr | 40 mTorr |
| Power | 0.3 kW | 0.15 kW |
| Substrate Temperature | 20° C. | 20° C. |
| Base Pressure | 3.0 × 10$^{-6}$ Torr | 3.0 × 10$^{-6}$ Torr |
| Anode/Cathode Distance | 100 mm | 100 mm |
| Sputtering Time | 7.5–9 min | 1.5 min |
| Voltage | 369–373 V | 346 V |

The resulting coating was blue in appearance. A fingertip touch was sufficient to cause a colour change to yellow. The base layer was about 900 nm thick, while the top layer was 100 nm thick.

A zone of inhibition test was conducted. Mueller Hinton agar was dispensed into Petri dishes. The agar plates were allowed to surface dry prior to being inoculated with a lawn of *Staphylocccus aureus* ATCC#25923. The inoculant was prepared from Bactrol Discs (Difco, M.) Which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition–diameter of the test material in contact with the agar). The results showed a corrected ZOI of about 10 mm.

The coating was analyzed by nitric acid digestion and atomic absorption analysis to contain 0.24+/–0.04 mg silver per mg high density polyethylene. The coating is a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies demonstrated that silver was released continuously from the coating until an equilibrium concentration of about 66 mg/L was reached (determined by atomic absorption), a level that is 50 to 100 times higher than is expected from bulk silver metal (solubility ≦1 mg/L).

By varying the coating conditions for the top layer to lengthen the sputtering time to 2 min, 15 sec. a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

Example 2

This example is included to demonstrate a multilayer transcutaneous device dressing in accordance with the present invention. High density polyethylene mesh dressing material DELNET™ or CONFORMANT 2™ dressing was coated with a bilayer blue anti-microbial coating as set forth in Example 1. using the sputtering conditions of Table 1. Two layers of this coated dressing material were placed above and below an absorbent core material formed from needle punched rayon/polyester (SONTARA™ 8411). With the silver coating on both the first and third layers, the dressing may be used with either the blue coating side or the silver side in the skin facing position. For indicator value, it might be preferable to have the blue coating visible. The three layers were laminated together by ultasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged in sealed individually polyester peelable pouches, and has shown a shelf life greater than 1 year in this form. The coated dressings can be cut in ready to use sizes, such as 5.1×10.2 cm strips, and slits formed therein before packaging. Alternatively, the dressings may be packaged with instructions for the clinician to cut the dressing to size and form the desired length of the slit for the medical device.

Example 3

This animal study evaluated four prototype catheter dressings, one of which was in made in accordance with Example 2 above, the others being 3 cm disc shaped catheter dressings of laminated dressing materials, having a thickness less than about 1 mm, formed with a slit to their center to fit beneath the catheter, and being coated with a silver coating deposited as in Example 1. The silver coatings were prepared in a full scale roll coater under conditions to provide coatings having the same properties set out in Examples 2 and 3 above.

The prototype dressings were as follows:
1. Silver Catheter Dressing, prepared as in Example 2, with a top and a bottom dressing sized 5.1×5.1 cm, with a 2.6 cm slit in the bottom dressing, as an example of this invention.
2. Silver Disc 1—A 3 cm disc of the dressing material of Example 2, but used only as a flat disc beneath the catheter (i.e., with no top dressing)
3. Silver Disc 2—A 3 cm disc of the dressing material which included a first layer of silver coated DELNET, as set out in Example 1, laminated to STATEX, AET, 8.0NP$_2$-A/QW, which is a layer of 100% rayon on a polyurethane film, used as a flat disc beneath the catheter (i.e. with no top dressing)
4. Silver Foam Disc 3—A 3 cm disc formed of three layers of silver coated high density polyethylene prepared as in Example 1, alternating with two layers of polyurethane foam, L-00562-6 Medical Foam, available from Rynel Ltd., Bootbay, Me., USA, used as a flat disc beneath the catheter (i.e., with no top dressing).

Fifteen healthy New Zealand white rabbits weighing 2.6 to 2.9 kg were used. Segments of polyurethane catheters (Arrow polyurethane indwelling central venous catheters, 16 Ga, from Arrow International, Inc., Reading, Pa., USA, cut to 5 cm long) were implanted subcutaneously in the back of the rabbits. The rabbits were anesthetized with halothane (University of Calgary, LESARC SOP A6—Life & Environmental Sciences Animal Resource Centre, Standard Operating Procedures). The dorsal thorax and abdomen were clipped and scrubbed with non-antibiotic soap. A scalpel was used to make a cut on the skin. A 5 cm long catheter segment was then inserted into subcutaneous tissue space perpendicular to the spine. Six catheters were implanted in each rabbit. The catheter sites were dressed with each of the prototype catheter dressings or control gauzes, such that the protruding portion of the catheter passed through the slit of the disc or dressing. In the case of the dressing of this invention, Silver Catheter Dressing, the top layer was placed over the catheter and pressed down so that the dressing surrounded the segment of the catheter protruding from the skin. The catheters were sutured to the skin. Three rabbits were dressed with each type of dressing or control dressing.

Bacterial challenges of each site were made by placing bacterial suspension-soaked gauzes (10×12.5 cm) on the tops of the dressings. In this inoculation technique the gauzes used were larger than the test dressings and were in contact with the heads of the catheters which protruded above the dressings, as a result the gauzes provided sources of bacteria to the surrounding skin, the catheter dressings and the catheter heads. Five milliliters of bacterial suspension (*Staphylococcus aureus* ATCC 25923, grown in TSB (tryptic soy broth) overnight, washed with PBS (phosphate buffered saline) and re-suspended in PBS, concentration adjusted to $10^7$ CFU/ml (colony forming unit)) was inoculated at each catheter site. An occlusive tape was then placed over the dressing to ensure a moist environment inside.

The rabbits were observed for seven days and then euthanized on Day 7. The skin was dissected and the inside portion of catheter was carefully exposed. Catheter sections (1 cm) were cut from the proximal and distal sites to the skin entrance and collected in tubes containing 2 ml of STS (0.4% sodium thioglycolate, 0.85% sodium chloride and 1% Tween™ 20). Adherent bacteria were recovered from the proximal and distal sites of the catheters by sonication and vortexing. The solutions were plated on TSA plates using a drop-plate method and bacterial counts were recorded.

During the whole test period, all dressings or discs remained in place, although some curling and folding occurred on three of the Disc 1 type discs. The results of the colonization rates and bacteria counts for the proximal and distal sites of the implanted catheters are presented in Table 2, with means of n (shown in parentheses) samples. The numbers in parenthesis following the colonization rates represent numbers of colonized/total catheters.

TABLE 2

Catheter Colonization Rates and Bacterial Recovery from Catheters

| Dressing Type | Colonization Rate (%) | Bacterial Counts for the Proximal Site (CFU/cm) | Bacterial Counts for the Distal Site (CFU/cm) |
|---|---|---|---|
| Silver Catheter Dressing | 0 (0/18) | 0 | 0 |
| Silver Disc 1 | 38.8 (7/18) | $1.8 \times 10^3$ (n = 7) | $5.8 \times 10^2$ (n = 9)* |
| Silver Disc 2 | 47.1 (8/17) | $4.6 \times 10^3$ (n = 8) | $3.2 \times 10^2$ (n = 6) |
| Silver Foam Disc 3 | 33.3 (6/18) | $1.4 \times 10^3$ (n = 6) | $3.0 \times 10^2$ (n = 2) |
| Control | 94.4 (17/18) | $7.6 \times 10^4$ (n = 17) | $4.1 \times 10^3$ (n = 11) |

*Two distal sites had 50 CFU/cm (only one colony was found in one of the duplicate plates, while the proximal sites of the same catheters had no bacteria). This may have been because of contamination. These two sites were not included when the colonization rate was calculated for this group.

The data showed that with gauze coverage, 94.4% of the catheters were contaminated with bacterial counts averaging over $10^4$ CFU/cm. With regard to the Silver Catheter Dressing of this invention, it completely prevented bacterial colonization. The disc type dressings, Discs 1, 2 and 3 reduced catheter contamination rates to 38.8%, 47% and 33.3%, respectively. It is expected that these disc dressing materials would reduce catheter contamination to a sufficiently low rate if a top dressing of the same material was used with the discs, in accordance with the present invention.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

We claim:

1. A transcutaneous device dressing for use with a transcutaneous medical device which has punctured the skin of a patient and which has a portion of the medical device protruding from the skin, comprising:
  a top and a bottom dressing, both being formed from a flexible material and having upper and lower surfaces, the lower surfaces being skin facing when the dressing in use;
  the bottom dressing having a slit formed therein extending from one edge inwardly to a termination point within the confines of the bottom dressing;
  an anti-microbial material provided without the use of adhesives at the upper and lower surfaces of the bottom dressing, and at least at the lower surface of the top dressing;
  whereby, in use, the bottom dressing is placed next to the skin, the slit allowing the bottom dressing to surround the puncture site such that the lower surface of the bottom dressing is in contact with the skin and the upper surface of the bottom dressing is in contact with a portion of the medical device protruding from the skin, and the top dressing is placed above the puncture site such that its lower surface is in contact with a portion of the medical device protruding from the skin, thereby exposing a portion of the medical device protruding from the skin from above and below to the anti-microbial activity of the anti-microbial material.

2. The dressing as set forth in claim 1, wherein:
  the top and bottom dressings are formed from a unitary dressing and are joined together and divided by a fold line.

3. The dressing as set forth in claim 2, wherein:
  the anti-microbial material is a coating of an anti-microbial metal applied to the upper and lower surfaces of the bottom dressing, and at least to the lower surface of the top dressing.

4. The dressing as set forth in claim 3, therein the slit is formed from the edge of the bottom dressing which is parallel to the fold line, such that the slit is generally perpendicular to the fold line.

5. The dressing as set forth in claim 4, wherein the top and bottom dressings are formed from multilayered, laminated dressing material.

6. The dressing as set forth in claim 5, wherein the top and bottom dressings are formed from:
  a first, skin facing layer formed of a perforated, non-adherent material; a second layer laminated to the first layer, and being formed of an absorbent material; and a third layer laminated to one or both of the first and second layers.

7. The dressing as set forth in claim 6, wherein the anti-microbial metal coating is formed on the first and the third layers.

8. The dressing as set forth in claim 7, wherein the top and bottom dressings are sized so as to provide coverage of the portion of the medical device protruding from the skin of at least about 5 mm.

9. The dressing as set forth in claim 8, therein the anti-microbial metal coating is a thin film containing at least one anti-microbial metal, said anti-microbial metal being formed with sufficient atomic disorder such that the thin film, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

10. The dressing as set forth in claim 9, therein the anti-microbial metal coating comprises:
  a base layer of a partly reflective material capable of generating an interference colour when covered with a partly reflective, partly light transmissive top layer;
    a top layer formed over said base layer, said top layer being a partly reflective, partly light transmissive thin film containing at least one anti-microbial metal and having a thickness such that a first or second order interference colour is produced, said top layer having a refractive index different from that of the base layer, and anti-microbial metal being formed with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

11. The dressing as set forth in claim 9, wherein the first and third layers are formed from a non-woven, perforated, non-adherent high density polyethylene material.

12. The dressing as set forth in claim 10, wherein the material in the base layer is a metal selected from the group consisting of Ag, Au, Pt, Pd, Cu, Ta, Al and alloys or compounds of one or more of these metals, in a partly reflective form, and wherein the anti-microbial metal in the top layer is selected from the group consisting of Ag, Au, Pt, Pd, Ir, Sn, Cu, Sb, Bi, Zn, and alloys or compounds of one or more of these metals.

13. The dressing as set forth in claim 12 wherein the material in the base layer and the anti-microbial metal in the top layer is a metal selected from the group consisting of Au, Ag, Pt, Pd, and Cu in a partly reflective form, and is formed by vapour deposition with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

14. The dressing of claim 13, wherein the metal in the base and top layer is Ag, Pt or Au.

15. The dressing as set forth in claim 14, wherein the top layer is a thin film of a composite material formed by co-, sequentially or reactively depositing the anti-microbial metal by vapour deposition in a matrix with atoms or molecules of a different material to create atomic disorder in the matrix, said different material being selected from the group consisting of biocompatible metals, oxygen, nitrogen, hydrogen, boron, sulphur or halogens, or an oxide, nitride, carbide, boride, halide, sulphide or hydride of either or both of an anti-microbial metal or a biocompatible metal.

16. The dressing as set forth in claim 15, wherein the biocompatible metal is selected from the group consisting of Ta, Ti, Nb, V, Hf, Zn, Mo, Si and Al.

17. The dressing as set forth in claim 16, wherein the anti-microbial metal is silver and said different material is one or both of silver oxide and atoms or molecules containing oxygen trapped or absorbed in the matrix.

18. The dressing as set forth in claim 17, wherein the top layer is less than 400 nm thick, and the base layer is at least 25 nm thick.

19. The dressing as set forth in claim 18, wherein the top layer is between 5 and 210 nm thick, and the base layer is at least 60 nm thick.

20. The dressing as set forth in claim 19, wherein the top layer is about 40–160 nm thick and the base layer is at least about 300 nm thick.

21. The dressing as set forth in claim 19, wherein the first and third layers are formed from a non-woven, perforated, non-adherent high density polyethylene material.

22. The dressing as set forth in claim 21, wherein the second layer is formed from a non-woven, absorbent rayon/polyester material.

23. A method of dressing the puncture site of a transcutaneous medical device to limit infection by microorganisms from the surrounding skin and a portion of the medical device that protrudes from the skin of a patient, comprising:
providing a transcutaneous device dressing, comprising:
a top and a bottom dressing, both being formed from a flexible material and having upper and lower surfaces, the lower surfaces being skin facing when the dressing is in use;
the bottom dressing having a slit formed therein extending from one edge inwardly to a termination point within the confines of the bottom dressing; and
an anti-microbial material provided without the use of adhesives at the upper and lower surfaces of the bottom dressing, and at least at the lower surface of the top dressing;
sliding the bottom dressing in place next to the skin using the slit to allow the bottom dressing to surround the puncture site at the termination point such that the lower surface of the bottom dressing is in contact with the skin surrounding the puncture site and the upper surface of the bottom dressing is in contact with a portion of the medical device protruding from the skin;
applying the top dressing above bottom dressing such that the lower surface of the top dressing is in contact with a portion of the medical device protruding from the skin;
depending on the anti-microbial material, applying a water or alcohol based electrolyte to the dressing to release the anti-microbial material; and
fixing the top and bottom dressings to the skin.

24. The method as set forth in claim 23, wherein:
the top and bottom dressings are formed from a unitary dressing and are joined together and divided by a fold line.

25. The method as set forth in claim 24, wherein:
the anti-microbial material is a coating of an anti-microbial metal applied to the upper and lower surfaces of the bottom dressing, and at least to the lower surface of the top dressing.

26. The method as set forth in claim 25, wherein the slit is formed from the edge of the bottom dressing which is parallel to the fold line, such that the slit is generally perpendicular to the fold line.

27. The method as set forth in claim 26, wherein the top and bottom dressings are formed from multilayered, laminated dressing materials.

28. The method as set forth in claim 27, wherein the top and bottom dressings are formed from:
a first, skin facing layer formed of a perforated, non-adherent material;
a second layer laminated to the first layer, and being formed of an absorbent material; and
a third layer laminated to one or both of the first and second layers.

29. The dressing or method as set forth in claim 28, wherein the anti-microbial metal coating is formed on the first and the third layers.

30. The method as set forth in claim 29, wherein the top and bottom dressings are sized so as to provide coverage of the portion of the medical device protruding from the skin of at least about 5 mm.

31. The method as set forth in claim 30, wherein the anti-microbial metal coating is a thin film containing at least one anti-microbial metal, said anti-microbial metal being formed with sufficient atomic disorder such that the thin film, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

32. The method as set forth in claim 31, wherein the anti-microbial metal coating comprises:
a base layer of a partly reflective material capable of generating an interference colour when covered with a partly reflective, partly light transmissive top layer;
a top layer formed over said base layer, said top layer being a partly reflective, partly light transmissive thin film containing at least one anti-microbial metal and having a thickness such that a first or second order interference colour is produced, said top layer having a refractive index different from that of the base layer, and anti-microbial metal being formed with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

33. The method as set forth in claim 32, wherein the material in the base layer is a metal selected from the group consisting of Ag, Au, Pt, Pd, Cu, Ta, Al and alloys or compounds of one or more of these metals, in a partly reflective form, and wherein the anti-microbial metal in the top layer is selected from the group consisting of Ag, Au, Pt, Pd, Ir, Sn, Cu, Sb, Bi, Zn, and alloys or compounds of one or more of these metals.

34. The method as set forth in claim 33, wherein the material in the base layer and the anti-microbial metal in the top layer is a metal selected from the group consisting of Au, Ag, Pt, Pd, and Cu in a partly reflective form, and is formed by vapour deposition with sufficient atomic disorder such that the top layer, in contact with an alcohol or water based electrolyte, releases ions, atoms, molecules or clusters of the anti-microbial metal into the alcohol or water based electrolyte at a concentration sufficient to provide a localized anti-microbial effect on a sustainable basis.

35. The method of claim 34 wherein the metal in the base and top layer is Ag, Pt or Au.

36. The method as set forth in claim 35, wherein the top layer is a thin film of a composite material formed by co-, sequentially or reactively depositing the anti-microbial metal by vapour deposition in a matrix with atoms or molecules of a different material to create atomic disorder in the matrix, said different material being selected from the group consisting of biocompatible metals, oxygen, nitrogen, hydrogen, boron, sulphur or halogens, or an oxide, nitride, carbide, boride, halide, sulphide or hydride of either or both of an anti-microbial metal or a biocompatible metal.

37. The method as set forth in claim 36 wherein the biocompatible metal is selected from the group consisting of Ta, Ti, Nb, V, Hf, Zn, Mo, Si and Al.

38. The method as set forth in claim 37, wherein the anti-microbial metal is silver and said different material is one or both of silver oxide and atoms or molecules containing oxygen trapped or absorbed in the matrix.

39. The method as set forth in claim 38, wherein the top layer is less than 400 nm thick, and the base layer is at least 25 nm thick.

40. The method as set forth in claim 39, herein the top layer is between 5 and 210 nm thick, and the base layer is at least 60 nm thick.

41. The method as set forth in claim 40, wherein the top layer is about 40–160 nm thick and the base layer is at least about 300 nm thick.

42. The method as set forth in claim 40, wherein the first and third layers are formed from a non-woven, perforated, non-adherent high density polyethylene material.

43. The method as set forth in claim 42, wherein the second layer is formed from a non-woven, absorbent rayon/polyester material.

44. The method as set forth in claim 31, wherein the first and third layers are formed from a non-woven, perforated, non-adherent high density polyethylene material.

45. The method as set forth in claim 23, wherein the dressing is fixed in place with an occlusive or semi-occlusive layer which maintains the dressing in a moist condition.

46. The method as set forth in claim 45, wherein the occlusive or semi-occlusive layer is an adhesive film.

* * * * *